United States Patent [19]

Kovács et al.

[11] Patent Number: 4,735,965

[45] Date of Patent: Apr. 5, 1988

[54] 7-OXO-PGI₂-EPHEDRINE SALTS AND THEIR PHARMACEUTICAL COMPOSITIONS AND METHODS

[75] Inventors: Gábor Kovács; Géza Galambos; István Tömösközi; Károly Kánai; Péter Györy; Péter Körmöczy; István Stadler, all of Budapest; Lászlo Szekeres, Szeged; Gyula Papp, Szeged; Éva Udvary, Szeged; Pál Hadházy, Budapest; Jenö Marton, Budapest; György Dormán, Budapest, all of Hungary

[73] Assignee: Chinoin Gyogyszer es Vegyeszeti Termekek Gyara Rt., Budapest, Hungary

[21] Appl. No.: 868,772

[22] Filed: May 28, 1986

[30] Foreign Application Priority Data

May 29, 1985 [HU] Hungary .............................. 2050/85

[51] Int. Cl.⁴ ................ A61K 31/557; C07D 307/935
[52] U.S. Cl. .................................... 514/469; 549/465
[58] Field of Search ......................... 549/465; 514/469

[56] References Cited

U.S. PATENT DOCUMENTS 4,330,553  5/1982  Simonidesz et al. ................ 549/465

OTHER PUBLICATIONS

Merck Index, 8th Ed. (1968), pp. 409–410, and 10th Ed. (1983), p. 3555.
Oki et al., Bull. Chem. Soc. Japan, 43 (1970) pp. 2554–2558.
Kovacs et al, J. Med. Chem., 25(2) (1982) pp. 105–108.

Primary Examiner—Henry R. Jiles
Assistant Examiner—Bernard I. Dentz
Attorney, Agent, or Firm—Karl F. Ross; Herbert Dubno

[57] ABSTRACT

The invention relates to new 7-oxo-PGI₂-ephedrine salt analogues of the Formula I

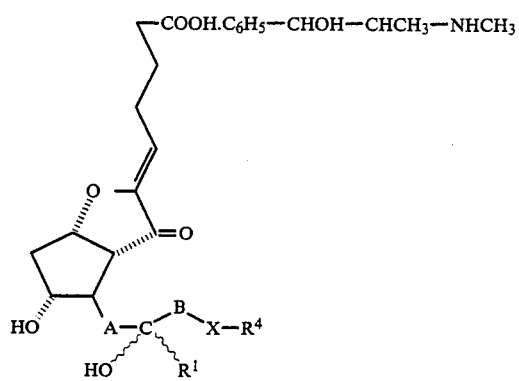

wherein
A stands for —(CH₂)₂—, cis or trans —CH=CH— or —C≡C—;
$R^1$ is lower alkyl or hydrogen;
B represents a chemical bond, —CH₂— or —CR²R³;
$R^2$ stands for lower alkyl or hydrogen;
$R^3$ represents lower alkyl or hydrogen;
X is a chemical bond, —O— or —CH₂—;
$R^4$ stands for $C_{1-6}$ alkyl, $C_{4-7}$ cycloalkyl, $C_{1-6}$ *fluoroalkyl*, $C_{2-6}$ alkenyl, $C_{2-6}$ alkynyl, phenyl, substituted phenyl or heteroaryl.

The salts of the Formula I show the same pharmacological profile as the sodium salt of PGI₂, they inhibit blood aggregation and the secretion of gastric acid, are useful in the prevention of anginal attacks. Accordingly the salts of the present invention are useful in the prevention of peripheral vascular diseases, in improving circulation of extremities, in relieving the seriousness of cardiac infarction and also in the treatment and prevention of gastrointestinal ulcer and acute or chronical liver injury.

9 Claims, No Drawings

7-OXO-PGI$_2$-EPHEDRINE SALTS AND THEIR PHARMACEUTICAL COMPOSITIONS AND METHODS

This invention relates to new salts, a process for the preparation thereof and pharmaceutical compositions comprising the same. More particularly it is concerned with new 7-oxo-PGI$_2$ ephedrine salts, a process for the preparation thereof and pharmaceutical compositions comprising the same.

According to the feature of the present invention there are provided new salts of the Formula I

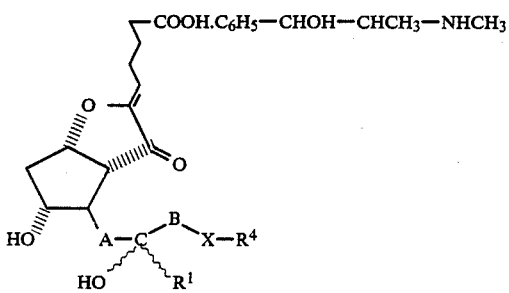

wherein
A stands for —(CH$_2$)$_2$—, cis or trans —CH=CH— or —C≡C—;
R$^1$ is lower alkyl or hydrogen;
B represents a chemical bond, —CH$_2$— or —CR$^2$R$^3$;
R$^2$ stands for lower alkyl or hydrogen;
R$^3$ represents lower alkyl or hydrogen;
X is a chemical bond, —O— or —CH$_2$—;
R$^4$ stands for C$_{1-6}$ alkyl, C$_{4-7}$ cycloalkyl, C$_{1-6}$ fluoroalkyl, C$_{2-6}$ alkenyl, C$_{2-6}$ alkynyl, phenyl, substituted phenyl or heteroaryl.

Particularly preferred representatives of the compounds of the Formula I are the following derivatives:
7-oxo-PGI$_2$-(−)-ephedrine salt
7-oxo-16,17,18,19,20-pentanor-15-cyclopentyl-PGI$_2$-(−)-ephedrine salt
7-oxo-PGI$_2$-(+)-ephedrine salt
7-oxo-16,17,18,19,20-pentanor-15-cyclopentyl-PGI$_2$-(+)-ephedrine salt
7-oxo-PGI$_2$-(+)-ephedrine salt
7-oxo-16,17,18,19,20-pentanor-15-cyclopentyl-PGI$_2$-(±)-ephedrine salt.

The new compounds of the Formula I have the same efficiency as 7-oxo-16,17,18,19,20-pentanor-15-cyclopentyl-PGI$_2$ and 7-oxo-PGI$_2$ known from prior art and salts thereof. In the synthesis of prostacyclin and generally prostaglandin analogs and in the preparation of pharmaceutical compositions comprising the same it is generally very difficult to obtain the said compounds in a form which is easy to handle and is preferably crystalline.

According to prior art it is sometimes preferable to prepare and use the metal and ammonium salts of the said compound group U.S. Pat. No. 3,706,789. The tris-(hydroxyamino)-methane (THAM) salts of PGF$_2$ and PGI$_2$ proved to be particularly advantageous (Belgian Pat. No. 767,926). The sodium salt of prostacyclin is readily crystallizable and easy to handle (European patent application No. 48,107).

The known crystallization methods are not applicable for 7-oxo-PGI$_2$ and derivatives thereof; this pertains to the methods disclosed in the cited patent specifications too. This is due to the fact that the salts formed are either not crystalline or unstable and the treatment and purification thereof is circumstantial.

We have prepared the salts of 7-oxo-PGI$_2$ formed with papaverin, triethyl amine, dicyclohexyl amine and tris-(hydroxymethylamino) (THAM). Said salts can not be prepared in crystalline form according to known methods by using water, alkanes, cycloalkanes, aromatic hydrocarbons, chlorinated hydrocarbons, ethers, esters or alcohols. The same result has been obtained with the sodium salt of 7-oxo-PGI$_2$.

We have isolated the calcium and magnesium salts of 7-oxo-PGI$_2$ by known methods (J. Org. Chem. page 5341 (1983)). The yellowish white salts thus obtained undergo to significant decomposition during drying and recrystallization, respectively and for this reason the use thereof is accompanied by several difficulties.

It has surprisingly been found that the compounds of the Formula I are stable crystalline substances which are very easy to handle and are readily soluble in water. Thus the new compounds of the Formula I can be efficiently purified and are highly useful as active ingredient of pharmaceutical compositions.

The easily crystallizable compounds of the Formula I can be converted into free 7-oxo-prostacyclin acids and can also be used as intermediate in the purification of said acids.

The new compounds of the Formula I of the present invention are stable analogs of prostacycline (PGI$_2$) and concerning the pharmacological profile are similar to the sodium salt of PGI$_2$. The pharmacology and therapeutical application of the sodium salt of prostacyclin is disclosed in detail in the prior art (Drugs of Today 19, 605 (1983) and citations referred to therein).

The practical use of prostacyclin is rendered difficult by the fact that this compound is extremely unstable (J. Chem. Soc., Chem. Commun. 1979, 129).

It is much more simple and efficient to use in therapy prostacyclin analogs having similar pharmacological activity and being stabilized by various methods (R. F. Newton and coll., Synthesis 1984, 449; R. Noyori, M. Suzuki, Angew. Chem., Int. Ed. Engl., 23, 847 (1984). According to a particularly preferred stabilization method of the sensitive structural unit of prostacyclin—namely the enolether functional group—the C-7 methylene group is converted into an oxo group which decreases the sensitivity of the molecule against hydrolysis due to the electron withdrawing and delocalization effect thereof (J. Med. Chem. 25, 105 (1982), U.S. Pat. No. 4,330,553, European patent application No. 163,305).

In the hitherto reported processes the free acid form and the sodium and tris-((hydroxymethyl)-aminomethane) salts (THAM) of 7-oxo-prostacyclin analogues are disclosed and it is very circumstantial and difficult to prepare said compounds in pure form and to handle the same.

According to a further feature of the present invention there is provided a process for the preparation of new compounds of the Formula I, wherein
A stands for —(CH$_2$)$_2$—, cis or trans —CH=CH— or —C≡C—;
R$^1$ is lower alkyl or hydrogen;
B represents a chemical bond, —CH$_2$— or —CR$^2$R$^3$;
R$^2$ stands for lower alkyl or hydrogen;
R$^3$ represents lower alkyl or hydrogen;
X is a chemical bond, —O— or —CH$_2$—;

$R^4$ stands for $C_{1-6}$ alkyl, $C_{4-7}$ cycloalkyl, $C_{1-6}$ fluoroalkyl, $C_{2-6}$ alkenyl, $C_{2-6}$ alkynyl, phenyl, substituted phenyl or heteroaryl, which comprises (a) removing from a compound of the Formula II

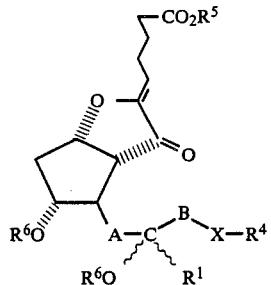

wherein $R^5$ stands for straight or branched chain lower alkyl; $R^6$ represents straight or branched chained lower alkanoyl, benzoyl or monosubstituted benzoyl and $R^1$, $R^2$, $R^3$, $R^4$, A, B and X are as stated above, the protecting groups with a base and thereafter removing the ester group by treatment with a base in the presence of water; or (b) removing from a compound of the Formula II wherein $R^6$ stands for hydrogen and $R^1$, $R^2$, $R^3$, $R^4$, A, B and X are as stated above, the ester group with the aid of a base in the presence of water, and thereafter treating the product with an acid and/or treating the extract of the reaction mixture thus obtained formed with a water non-miscible solvent or treating (c) a solution of a compound of the Formula II wherein $R^5$ and $R^6$ stand for hydrogen and $R^1$, $R^2$, $R^3$, $R^4$, A, B and X are as stated above, formed with a polar solvent with optically active or racemic ephedrine at a temperature between −20° C. and 50° C. and crystallizing the compound of the general Formula I thus obtained.

Salt formation may be carried out in a polar solvent (e.g. alcohols particularly ethanol; esters preferably ethyl acetate, ethers, preferably diethyl ether; acetone or dimethyl formamide) and preferably at room temperature. It is preferred to use 1.05–5.0 equivalents—particularly 1.1 equivalents—of optically active or racemic ephedrine. One may either proceed by directly subjecting the mixture thus obtained to crystallization or treat the solution first with a solvent in which the ephedrine salt is but poorly soluble e.g. an aliphatic hydrocarbon, particularly pentane, hexane, cyclohexane; an aromatic hydrocarbon, preferably benzene, toluene, xylene; a chlorinated hydrocarbon, particularly chloroform or carbon tetrachloride) and carry out crystallization thereafter.

It is not necessary to use purified compounds of the Formula II, wherein $R^5$ and $R^6$ are hydrogen and the other substituents are as stated above, in the preparation of the compounds of the Formula I. If compounds of the Formula II are used in which $R^5$ stands for lower alkyl and $R^6$ represents hydrogen, straight or branched chained alkanoyl, benzoyl or substituted benzoyl and the further substituents have the same meaning as stated above, one may also proceed by removing the above $R^6$ protecting groups, if desired, by methods well-known per se (e.g. by using a base, preferably an alkali carbonate, particularly potassium carbonate, under anhydrous conditions, or in the presence of water in a solvent, preferably an alcohol, particularly anhydrous methanol) and thereafter if necessary—i.e. if $R^5$ is other than hydrogen—hydrolizing the $R^5$ group by methods well-known per se, (e.g. with a base, preferably an alkali hydroxide, particularly sodium hydroxide in a water-miscible solvent, preferably an alcohol, particularly methanol, in the presence of water). The reaction mixture thus obtained is acidified with an inorganic acid (preferably hydrochloric acid, sulfuric acid, phosphoric acid, sodium bisulfite) to a pH value between 3 and 6 and the anhydrous solution of the compound of the Formula II thus obtained is introduced without purification to the salt formation reaction step which is carried out as described above.

The starting materials of the Formula II are known compounds (J. Med. Chem. 25, 105 (1982); U.S. Pat. No. 4,330,553; European patent application No. 163,905).

The compounds of the Formula I are suitable for the purification of 7-oxo-PGI$_2$ analog since said compounds may be converted into free acid by treatment with an acid or into the corresponding salt by reacting same with a base.

The pharmacological effects of the compounds of the Formula I are discussed above.

The pharmacological profile of the compounds of the present invention is the same that of prostacyclin, while the efficiency thereof is identical with that of other forms (e.g. free acid, sodium salt) of the corresponding 7-oxo-PGI$_2$ analog.

Thus the in vitro blood aggregation inhibiting effect of 7-oxo-16,17,18,19,20-pentanor-15-cyclopentyl-PGI$_2$ against 2 μM of ADP amounts to IC$_{50}$=0.003 nmole/ml both for the known sodium salt and the new ephedrine salt according to the present invention; the results are measured on plasma enriched in blood platelets according to the method of Born. The tests directed to the haemodinamic properties give similar results; on cat under i.v. bolus administration the blood pressure decreasing effect of the sodium salt amounts to 21.2 μg/kg, 40.3 nmole/kg; and that of the ephedrine salt is 29.0 μg/kg, 42.5 nmole/kg (ED$_{50}$).

It appears from the above data that the new compounds of the Formula I when administered in the same dose exhibit the same pharmacological effect as other salts.

In addition to the aforesaid the new compounds of the Formula I inhibit in the gastrointestinal tract the secretion of gastric acid on rats; exert cytoprotective effect i.e. reduce the number and relieve the seriousness of ulcer induced by alcohol, stress or indomethacin. In the cardiovascular system the compounds of the present invention decrease the oxygen demand of the heart in case of cardiac insufficiency on dogs, thus they inhibit the formation of anginal attacks and mitigate the strength of the seizure.

On rat liver the compounds of the Formula I eliminate lesions induced by carbon tetrachloride and inhibit the formation of injury, respectively. In accordance with the above pharmacological profile the compounds of the Formula I may be successfully applied on the same therapeutical fields as the sodium salt of prostacyclin or other known salts of 7-oxo-prostacyclin. Thus the compounds of the present invention are suitable for the inhibition of blood aggregation in extracorporal circulation. The compounds of the Formula I may be successfully used to prevent such diseases as peripherial vascular lesion; to improve circulation of the extremities; and in case of cardiac infection to relieve the severity of infarction i.e. to decrease death rate. In certain anginal diseases the compounds of the general Formula I are capable of decreasing the number and strength of the attacks.

Various cytoprotective effects of the compounds of the present invention may be utilized in the treatment and prevention of gastrointestinal ulcer diseases, acute and chronical liver injury.

On patients suffering from tumors the compounds of the Formula I exhibit metastasis inhibiting effect and thus increase survival.

The compounds of the Formula I may be used in the form of pharmaceutical compositions suitable for intravenous, subcutaneous or oral (gastrointestinal) administration. The effective dose may be generally between 0.0001 and 10 mg/kg depending from the age, body weight and sex of the patient and also from the type and seriousness of the disease.

According to a further feature of the present invention there are provided pharmaceutical compositions comprising as active ingredient at least one compound of the Formula I in admixture with suitable inert carriers and/or other excipients.

The said pharmaceutical compositions may be e.g. tablets, capsules or liquid formulations. The pharmaceutical compositions contain usual carriers, filling or binding agents or other excipients and may be prepared by method of pharmaceutical industry known per se.

The pharmaceutical compositions of the present invention may also comprise one or more further pharmaceutically active ingredients in addition to the compound of the general Formula I.

Further details of the present invention are to be found in the following Examples without limiting the scope of protection to the said Examples.

EXAMPLE 1

7-oxo-prostacyclin-(—)-ephedrine salt

CI; A=trans vinylene; $R^1$=H; B=X=chemical bond; $R^4$==n-penthyl.

1.83 g (5.0 millimoles) of 7-oxo-prostacyclin (II: $R^1$=$R^5$=$R^6$=H; A=trans vinylene; B=X=chemical bond; $R^4$=n-penthyl) are dissolved in 15 ml of anhydrous ethyl acetate and 0.825 g (5.0 millimoles) of (—)-ephedrine or a solution thereof formed with 5 ml of anhydrous ethyl acetate is added under stirring. The reaction mixture is stirred for an hour and allowed to stand in a refrigerator for 10-12 hours. The precipitated product is filtered, washed with a cold 3:1 mixture of hexane and ethyl acetate and dried. Thus 1.86 g of the desired compound are obtained.

mp: 121° C.,

TLC: after acidification in the form of the free acid $R_f$=0.34 (20:10:1 mixture of benzene, dioxane and acetic acid).

$^1$HNMR /methanol $d_4$/: 5.55 /2H, m/, 5.31 /1H, t/, 5.10 /2H, m/, 4.00 /2H, m/.

EXAMPLE 2

7-oxo-16,17,18,19,20-pentanor-15-cyclopentyl-PGI$_2$-(—)-ephedrine salt (I; A=trans vinylene: $R^1$=H; B=X=chemical bond; $R^4$==cyclopentyl)

To a solution of 467 mg (1 millimole) of 7-oxo-11,15-diacetyl-16,17,18,19,20-pentanor-15-cyclopentyl-PGI$_2$-methyl ester (II; $R^5$=CH$_3$, $R^6$=acetyl; the other symbols are as stated in the title) and 25 ml of methanol 0.5 ml (0.5 millimole) of a 1M methanolic sodium methylate solution is added. The reaction mixture is stirred at room temperature overnight and partially evaporated. To the residue 3.5 ml of a 1N sodium hydroxide solution are added and the mixture is stirred at 40° C. for an hour. The methanol is removed in vacuo, the residue is dissolved in 30 ml of water and washed twice with 5 ml of ether each. The ethereal phase is discarded, the aqueous layer is acidified with a 1N sodium hydrogen sulfate solution to the pH value of 6, and extracted twice with 20 ml of ethyl acetate each. The pH of the aqueous phase is adjusted to 4 with a 1N sodium hydrogen sulfate solution and extracted again twice with 20 ml of ethyl acetate each. The united ethyl acetate phases are extracted twice with 10 ml of a saturated sodium chloride solution each, stirred over magnesium sulfate for about 30 minutes, filtered and the filtrate is concentrated to about 5 ml in vacuo. To the solution 171 mg (0.93 millimoles) of (—)-ephedrine are added. The mixture is allowed to stand for 24 hours and crystallized with the aid of a mixture of hexane and ethyl acetate. Thus 113 mg of the desired compound are obtained, in the form of white crystals.

Mp.: 115°–120° C.

TLC: after acidification in the form of the acid $R_f$=0.30 (a 20:10:1 mixture of benzene, dioxane and acetic acid)

UV: $\lambda_{max}$=288 nm, 1 g$\epsilon$=3.890

EXAMPLE 3

7-oxo-13,14-didehydro-16,17,18,19,20-pentanor-15-cyclohexyl-PGI$_2$-(—)-ephedrine salt (I; A=—C≡C—; $R^1$=H; B=X=chemical bond; $R^4$=cyclohexyl) To a solution of 500 mg (1.1 millimoles) of 7-oxo-13,14-didehydro-11,15-diacetyl-16,17,18,19,20-pentanor-15-cyclohexyl-PGI$_2$-methyl ester (II; A=—C≡C—; $R^1$=H; B=X—chemical bond; $R^4$=cyclohexyl; $R^5$=methyl; $R^6$=acetyl) and 50 ml of methanol 0.5 ml (0.5 millimole) of a 1M methanolic sodium methylate solution is added. The reaction mixture is allowed to stand overnight and methanol is partially removed in vacuo. The residue is stirred with 4 ml of a sodium hydroxide solution at 40° C. for an hour. The reaction mixture is worked up as described in Example 2. Salt formation is carried out by using 180 mg (0.98 millimole) of (—)-ephedrine. One proceeds as described in Example 2. Thus 218 mg of the desired compound are obtained in the form of white crystals.

Mp.: 125°–128° C.

TLC: after acidification, in the form of the free acid,
$R_f$=0.30 (a 20:10:1 mixture of benzene, dioxane and acetic acid).

EXAMPLE 4

7-oxo-PGI$_2$-(—)-ephedrine salt (I; A=trans vinylene; $R^1$=H; B=X=chemical bond; $R^4$=n-pentyl)

1.1 g of (2.9 millimoles) of 7-oxo-prostacyclin-methyl ester (II; $R^5$=CH$_3$; $R^6$=H; the other symbols are as stated in the title) are dissolved in a mixture of 10 ml of methanol and 8 ml of a 1N sodium hydroxide solution. The reaction mixture is stirred at room temperature for 3 hours and the methanol is removed in vacuo. The residue is dissolved in 50 ml of water and washed twice with 10 ml of ether each. The aqueous layer is acidified with a 1N sodium hydrogen sulfate solution at 0° C. to pH 4 and extracted three times with 50 ml of ethyl acetate each. The united ethyl acetate phases are washed twice with 20 ml of a saturated sodium chloride solution each, and dried over anhydrous sodium sulfate. After removal of the drying agent the total volume is decreased to 5–10 ml and 462 mg (2.8 millimoles) of (—)-ephedrine are added. The reaction mixture is allowed to stand for 24 hours and crystallized from a mixture of hexane and ethyl acetate. Thus 958 mg of the desired compound are obtained. The physical constants of the product are identical with those of the compound prepared according to Example 1.

EXAMPLE 5

7-oxo-16,16-dimethyl-PGI$_2$-(—)-ephedrine salt (X; A=trans vinylene; R$^1$=H; B=—CR$^2$R$^3$—; X=chemical bond; R$^2$=R$^3$=methyl; R$^4$=n-pentyl)

608 mg (1.5 millimole) of 7-oxo-16,16-dimethyl-PGI$_2$-methyl ester (II; R$^5$=methyl; R$^6$=hydrogen; the other symbols are as stated in the title) are dissolved in a mixture of 8 ml of methanol and 7 ml of a 1N sodium hydroxide solution and the reaction mixture is hydrolysed at 40° C. for an hour. The reaction mixture is worked up as described in Example 4. Salt formation is carried out by using 231 mg (1.4 millimoles) of (—)-ephedrine. Crystallization is carried out by using ethyl acetate. The product is crystallized from ethyl acetate. Thus 420 mg of the desired compound are obtained in the form of white crystals.

Mp.: 113°–117° C.

UV: λ$_{max}$=290 nm, 1 gε=3.885

TLC: after acidification in the form of the free acid R$_f$=0.48 (in the form of a 20:10:1 mixture of benzene, dioxane and acetic acid).

What we claim is:

1. An 7-oxo-PGI$_2$ ephedrine salt of the Formula I,

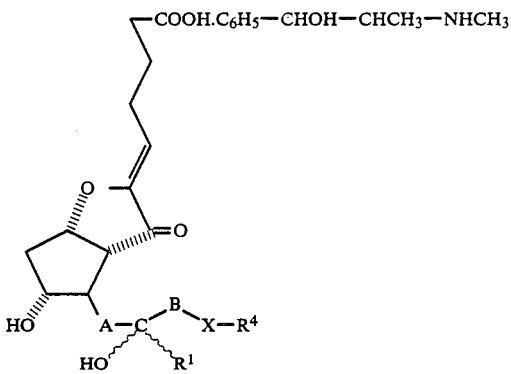

wherein

A stands for —(CH$_2$)$_2$—, cis or trans —CH=CH— or —C≡C—;
R$^1$ is lower alkyl or hydrogen;
B represents a chemical bond, —CH$_2$— or CR$^2$R$^3$;
R$^2$ stands for lower alkyl or hydrogen;
R$^3$ represents lower alkyl or hydrogen;
X is a chemical bond, —O— or —CH$_2$—;
R$^4$ stands for C$_{1-6}$ alkyl, C$_{4-7}$ cycloalkyl, C$_{1-6}$ fluoroalkyl, C$_{2-6}$ alkenyl, C$_{2-6}$ alkynyl or phenyl.

2. 7-oxo-PGI$_2$-(—)-ephedrine salt as defined in claim 1.

3. 7-oxo-16,17,18,19,20-pentanor-15-cyclopentyl-PGI$_2$-(—)-ephedrine salt as defined in claim 1.

4. 7-oxo-PGI$_2$-(—)-ephedrine salt as defined in claim 1.

5. 7-oxo-16,17,18,19,20-pentanor-15-cyclopentyl-PGI$_2$-(+)-ephedrine salt as defined in claim 1.

6. 7-oxo-PGI$_2$-(±)-ephedrine salt.

7. 7-oxo-16,17,18,19,20-pentanor-15-cyclopentyl-PGI$_2$-(±)-ephedrine salt.

8. A pharmaceutical composition for PGI$_2$ type therapy consisting essentially of a compound of claim 1 in admixture with suitable inert pharmaceutical carriers and/or excipients.

9. A method of treating a subject responsive to PGI$_2$ type therapy which comprises administering an effective amount of a compoound as defined in claim 1.

* * * * *